United States Patent
Godo

(10) Patent No.: US 10,986,985 B2
(45) Date of Patent: Apr. 27, 2021

(54) CAPSULE ENDOSCOPE SYSTEM

(71) Applicant: OLYMPUS CORPORATION, Tokyo (JP)

(72) Inventor: Hirokazu Godo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 338 days.

(21) Appl. No.: 15/917,925

(22) Filed: Mar. 12, 2018

(65) Prior Publication Data
US 2018/0199800 A1 Jul. 19, 2018

Related U.S. Application Data

(63) Continuation of application No. PCT/JP2016/053196, filed on Feb. 3, 2016.

(30) Foreign Application Priority Data

Sep. 17, 2015 (WO) ................. PCT/JP2015/076437

(51) Int. Cl.
*A61B 1/00* (2006.01)
*A61B 1/04* (2006.01)
(Continued)

(52) U.S. Cl.
CPC .......... *A61B 1/041* (2013.01); *A61B 1/00006* (2013.01); *A61B 1/00009* (2013.01);
(Continued)

(58) Field of Classification Search
CPC ............................. A61B 1/041; A61B 1/0006
(Continued)

(56) References Cited

U.S. PATENT DOCUMENTS 6,709,387 B1 * 3/2004 Glukhovsky ...... A61B 1/00009
348/399.1
2008/0242926 A1 10/2008 Nishino
2012/0271104 A1 * 10/2012 Khait .................... A61B 1/041
600/109

FOREIGN PATENT DOCUMENTS

JP 2008-220522 A 9/2008
JP 2008-237640 A 10/2008
(Continued)

OTHER PUBLICATIONS

International Search Report dated Apr. 12, 2016 issued in PCT/JP2016/053196.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A capsule endoscope system includes a capsule endoscope and a wireless communication device. The capsule endoscope includes a first movement sensor, a determiner, an imager, and a first wireless receiver. The wireless communication device includes a second analyzer and a first wireless transmitter. The first analyzer analyzes first data and generates a first analysis result. The second analyzer analyzes second data and generates a second analysis result. The determiner determines an imaging timing at a period that is equal to or shorter than a reception period on the basis of any one of the first analysis result and the second analysis result.

9 Claims, 6 Drawing Sheets

(51) Int. Cl.
*A61B 5/06* (2006.01)
*A61B 1/045* (2006.01)

(52) U.S. Cl.
CPC ...... *A61B 1/00016* (2013.01); *A61B 1/00032* (2013.01); *A61B 1/00036* (2013.01); *A61B 1/045* (2013.01); *A61B 5/067* (2013.01)

(58) Field of Classification Search
USPC .................................................. 600/109, 118
See application file for complete search history.

(56) References Cited

FOREIGN PATENT DOCUMENTS

| | | | |
|---|---|---|---|
| JP | 2009-195271 A | | 9/2009 |
| JP | 2009195271 A | * | 9/2009 |
| JP | 2013-511320 A | | 4/2013 |
| JP | 2016-019707 A | | 2/2016 |
| WO | WO 2011/061746 A1 | | 5/2011 |
| WO | WO 2015/056475 A1 | | 4/2015 |
| WO | WO 2016/021044 A1 | | 2/2016 |

OTHER PUBLICATIONS

International Search Report dated Dec. 15, 2015 issued in PCT/JP2015/076437.

* cited by examiner

CAPSULE ENDOSCOPE SYSTEM

This application claims priority to and the benefit of International Application No. PCT/JP2015/076437 filed on Sep. 17, 2015, and is a continuation application of International Application No. PCT/JP2016/053196 filed on Feb. 3, 2016, the contents of which are incorporated by reference herein.

BACKGROUND OF THE INVENTION

Field of the Invention

The present invention relates to a capsule endoscope system.

Description of Related Art

When a capsule endoscope passes through an organ of a subject, the capsule endoscope moves relative to a human body. When a movement speed thereof is high, it is desirable for the capsule endoscope to increase an imaging frame rate to reduce a possibility of missing imaging of the subject. Furthermore, when the capsule endoscope is relatively stationary with respect to the human body, it is desirable for the capsule endoscope to decrease an imaging frame rate to reduce power consumption.

The system described in the U.S. Pat. No. 6,709,387 determines an imaging frame rate on the basis of an output of a sensor configured to detect movement of a capsule. In such a system, an imaging frame rate can also be determined on the basis of a comparison result of two images output from the capsule. A device outside of the capsule determines a frame rate and instructs the capsule on the determined frame rate.

The system described in Japanese Unexamined Patent Application, First Publication No. 2009-195271 includes two acceleration sensors. An acceleration sensor provided in a capsule endoscope detects an acceleration of a capsule endoscope. An acceleration sensor provided in a receiving device detects an acceleration of a human body into which the capsule endoscope has been input. The system described in Japanese Unexamined Patent Application, First Publication No. 2009-195271 detects a relative movement of the capsule endoscope with respect to the human body on the basis of outputs of the two acceleration sensors. In the system described in Japanese Unexamined Patent Application, First Publication No. 2009-195271, at least one of the capsule endoscope and the receiving device includes a determination means for determining an imaging frame rate on the basis of the detected movement.

SUMMARY OF THE INVENTION

According to a first aspect of the present invention, a capsule endoscope system includes a capsule endoscope and a wireless communication device. The capsule endoscope includes a first movement sensor, a determiner, an imager, and a first wireless receiver. The first movement sensor detects movement of the capsule endoscope and generates first data indicating the detected movement of the capsule endoscope. The first analyzer analyzes the first data and generates a first analysis result. The determiner determines an imaging timing. The imager performs imaging at the imaging timing determined by the determiner and acquires an image. The first wireless receiver receives a second analysis result from the wireless communication device. The wireless communication device includes a second analyzer and a first wireless transmitter. The second analyzer analyzes second data different in kind from the first data or detected from an object different from that from which the first data is detected and generates the second analysis result. The first wireless transmitter transmits the second analysis result to the capsule endoscope. The first analyzer outputs the first analysis result at a first period that is equal to or shorter than a reception period at which the first wireless receiver receives the second analysis result. The first analysis result and the second analysis result are input to the determiner. The determiner determines the imaging timing at a second period that is equal to or shorter than the reception period on the basis of any one of the first analysis result and the second analysis result.

According to a second aspect of the present invention, in the first aspect, the second analyzer may further generate instruction data to designate any one of the first analysis result and the second analysis result on the basis of the second analysis result. The first wireless transmitter may further transmit the instruction data to the capsule endoscope. The first wireless receiver may further receive the instruction data from the wireless communication device. The instruction data may be input to the determiner. The determiner may select any one of the first analysis result and the second analysis result on the basis of the instruction data.

According to a third aspect of the present invention, in the first aspect, the wireless communication device may further include a second movement sensor configured to detect movement of a human body in which the capsule endoscope is placed and generate second data indicating the detected movement of the human body. According to a fourth aspect of the present invention, in the third aspect, the capsule endoscope may further include a second wireless transmitter configured to transmit the first data to the wireless communication device. The wireless communication device may further include a second wireless receiver configured to receive the first data from the capsule endoscope. The second analyzer may further analyze the first data and the second data.

According to a fifth aspect of the present invention, in the first aspect, the capsule endoscope may further include a second wireless transmitter configured to transmit the image to the wireless communication device. The wireless communication device may further include a second wireless receiver configured to receive the image from the capsule endoscope. The second analyzer may further analyze the image. The image may be the second data.

According to a sixth aspect of the present invention, in the first aspect, the capsule endoscope may further include a battery configured to supply electric power to the first movement sensor, the first analyzer, the determiner, the imager, and the first wireless receiver. The wireless communication device may further include an estimator configured to estimate a remaining capacity of the battery and generate the second data indicating the estimated remaining capacity.

According to a seventh aspect of the present invention, in the first aspect, the wireless communication device may further include an estimator configured to estimate a position of the capsule endoscope and generate second data indicating the estimated position.

According to an eighth aspect of the present invention, in the first aspect, the capsule endoscope may further include a third analyzer configured to analyze the image acquired by the imager and generate a third analysis result. The third analysis result may be input to the determiner. The determiner may determine the imaging timing at the second period on the basis of any one of the first analysis result, the second analysis result, and the third analysis result.

DETAILED DESCRIPTION OF THE INVENTION

Embodiments of the present invention will be described with reference to the drawings. Generally, there is a large restriction on the size and power consumption of a capsule endoscope. For this reason, it is difficult for the capsule endoscope to perform a complex calculation. In order to respond immediately to movement of the capsule endoscope, the capsule endoscope can internally perform a simple analysis on an output of a movement sensor. However, it is difficult for the capsule endoscope to perform an analysis based on data acquired outside of the capsule endoscope or an advanced analysis based on data acquired by the capsule endoscope. In each embodiment of the present invention, a simple analysis in the capsule endoscope and an advanced analysis outside of the capsule endoscope can be performed together.

First Embodiment

Figure 1:
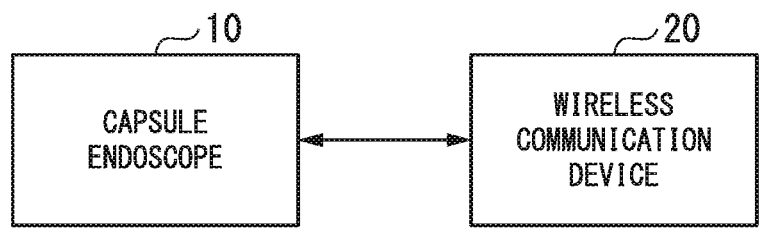
FIG. 1 is a block diagram showing a configuration of a capsule endoscope system according to a first embodiment of the present invention.

FIG. 1 shows a configuration of a capsule endoscope system 1 according to a first embodiment of the present invention. As shown in FIG. 1, the capsule endoscope system 1 includes a capsule endoscope 10 and a wireless communication device 20. The capsule endoscope 10 is placed in a human body. The wireless communication device 20 is placed outside of the human body. The capsule endoscope 10 and the wireless communication device 20 perform wireless communication.

Figure 2:
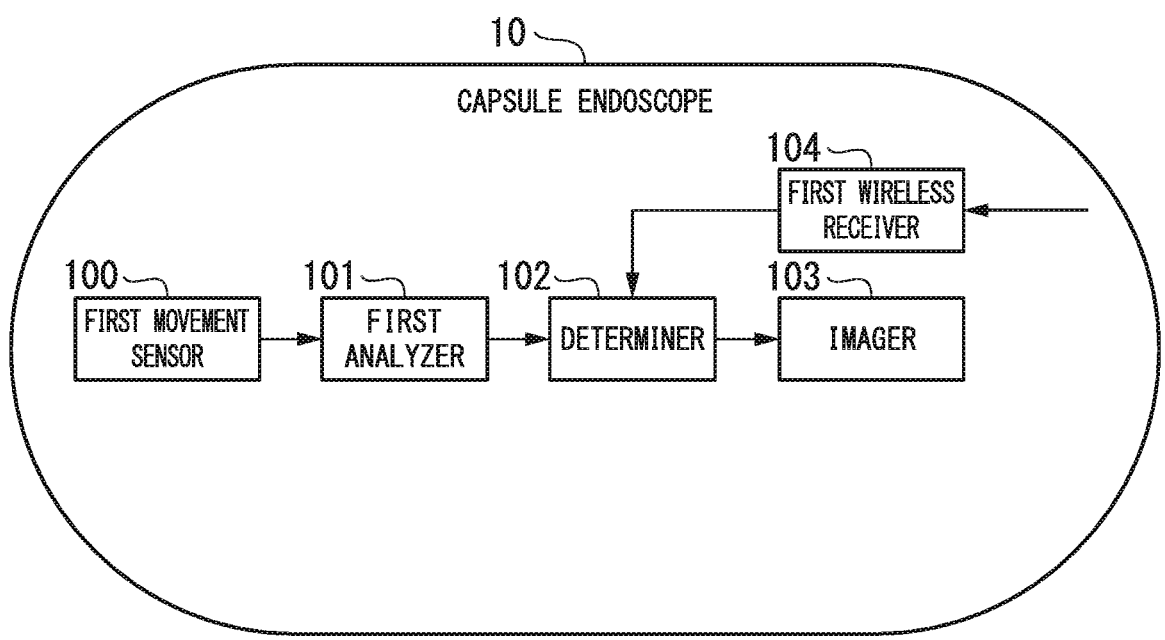
FIG. 2 is a block diagram showing a configuration of a capsule endoscope according to the first embodiment of the present invention.

FIG. 2 shows a configuration of the capsule endoscope 10. As shown in FIG. 2, the capsule endoscope 10 includes a first movement sensor 100, a first analyzer 101, a determiner 102, an imager 103, and a first wireless receiver 104.

The first movement sensor 100 detects movement of the capsule endoscope 10 and generates first data indicating the detected movement of the capsule endoscope 10. For example, the first movement sensor 100 may be at least one of an acceleration sensor, a speed sensor, a magnetic sensor, and an angular velocity sensor. Therefore, the first movement sensor 100 can acquire at least one of acceleration, speed, angular velocity, and magnetism data. The first movement sensor 100 outputs the first data to the first analyzer 101.

When the first movement sensor 100 is an acceleration sensor, the first data is acceleration data. The acceleration data is measurement results of the acceleration of the capsule endoscope 10

When the first movement sensor 100 is a speed sensor, the first data is speed data. The speed data is measurement results of the speed of the capsule endoscope 10.

Position data may be obtained by integrating speeds indicated by speed data. The movement of the capsule endoscope 10 can be detected from the amount of change of position data at a plurality of times.

When the first movement sensor 100 is a magnetic sensor, the first data is magnetic data. The magnetic data is measurement results of geomagnetism. The posture of the capsule endoscope 10 can be detected by using a magnetic sensor capable of performing measurement in directions in three dimensions. Therefore, the movement of the capsule endoscope 10 can be detected from the amount of change of magnetic data at a plurality of times.

When the first movement sensor 100 is an angular velocity sensor, the first data is angular velocity data. The angular velocity data is measurement results of the angular velocity of the capsule endoscope 10.

The first analyzer 101 analyzes the first data and generates a first analysis result. The first analyzer 101 is a processor such as a central processing unit (CPU) or a digital signal processor (DSP), or hardware such as an application specific integrated circuit (ASIC) or a field-programmable gate array (FPGA). The first analyzer 101 outputs the first analysis result to the determiner 102.

For example, when the first data is acceleration data or angular velocity data, the first analyzer 101 compares the first data with a predetermined threshold value. When the first data is any one of speed data, position data, and magnetic data, the first analyzer 101 compares the amount of change of the first data at a plurality of times with the predetermined threshold value. When the first data is acceleration data, the first analyzer 101 may calculate speed data or position data on the basis of the acceleration data. The first analysis result is a result of the above comparison.

The first wireless receiver 104 receives a second analysis result from the wireless communication device 20. The second analysis result is an analysis result of data in the wireless communication device 20. The first wireless receiver 104 further receives instruction data to designate any one of the first analysis result and the second analysis result from the wireless communication device 20. The first wireless receiver 104 outputs the second analysis result and the instruction data to the determiner 102. The first wireless receiver 104 is a wireless communication circuit.

The determiner 102 determines imaging timings on the basis of any one of the first analysis result and the second analysis result. The determiner 102 determines imaging timings of a plurality of frames by determining an imaging frame rate. The determiner 102 selects any one of the first analysis result and the second analysis result on the basis of the instruction data. The instruction data designates an analysis result selected by the determiner 102 between the first analysis result and the second analysis result. When the first analysis result is selected, the determiner 102 determines imaging timings on the basis of the first analysis result. When the second analysis result is selected, the determiner 102 determines imaging timings on the basis of the second analysis result. The determiner 102 is a processor such as a CPU or a DSP, or hardware such as an ASIC or an FPGA. A single piece of hardware including the first analyzer 101 and the determiner 102 may be provided.

The imager 103 performs imaging at imaging timings determined by the determiner 102 and acquires an image (image data). In other words, the imager 103 performs imaging at a frame rate determined by the determiner 102. The imager 103 is an imaging device. A subject, an image of which is captured by the imager 103 is an organ in the human body. An image acquired by the imager 103 may be transmitted to the wireless communication device 20.

The first movement sensor 100 generates first data at a first period. The first data is input to the first analyzer 101 at the first period. The first analyzer 101 generates a first analysis result at the first period. The first analysis result is input to the determiner 102 at the first period. The first wireless receiver 104 receives a second analysis result at a predetermined reception period. The first period is equal to or shorter than the reception period. That is, an interval at which the first analysis result is generated is equal to or shorter than an interval at which the second analysis result is received. In other words, the first analysis result is generated at a frequency equal to or higher than a reception frequency of the second analysis result. The second analysis result is input to the determiner 102 at the reception period. The determiner 102 determines imaging timings at a second period equal to or shorter than the reception period. For example, the first period and the second period may be the same. The first period and the second period are equal to or shorter than an imaging period in the imager 103. That is, the interval at which the first analysis result is generated and the interval at which the second analysis result is received are equal to or shorter than an imaging interval. In other words, the first analysis result is generated at a frequency equal to or higher than an imaging frequency and the second analysis result is received at a frequency equal to or higher than the imaging frequency. The reception period may be the same as the imaging period. The determiner 102 may determine an imaging timing at a second period equal to or shorter than the imaging period. The first analyzer 101 may generate the first analysis result at the first period and the first movement sensor 100 may generate first data at a period shorter than the first period.

For example, functions of the first analyzer 101 and the determiner 102 can be realized as software functions by using a computer of the capsule endoscope 10 reading and executing a program containing commands used for defining operations of the first analyzer 101 and the determiner 102. Such a program may be provided by, for example, a "computer readable recording medium" such as a flash memory. Furthermore, the above program may be transmitted from a computer including a storage device or the like in which such a program is stored in the capsule endoscope 10 via a transmission medium or by using a transmission wave in the transmission medium. A "transmission medium" configured to transmit a program is a medium having a function of transmitting information like a network (a communication network) such as the Internet or a communication circuit (a communication line) such as a telephone circuit. Furthermore, the above program may realize a part of the above-described functions. In addition, the above program may be a differential file (a differential program) which can realize the above-described functions in combination with a program recorded in advance in the computer.

Figure 3:
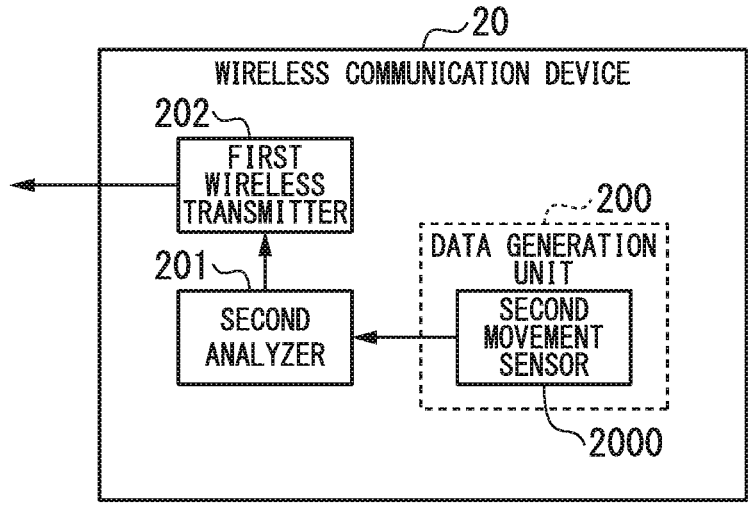
FIG. 3 is a block diagram showing a configuration of a wireless communication device according to the first embodiment of the present invention.

FIG. 3 shows a configuration of the wireless communication device 20. As shown in FIG. 3, the wireless communication device 20 includes a data generation unit 200, a second analyzer 201, and a first wireless transmitter 202.

The data generation unit 200 generates the second data. The second data is different in kind from the first data. Alternatively, the second data is data detected from an object different from that from which the first data is detected. The data generation unit 200 includes a second movement sensor 2000. The second movement sensor 2000 detects the movement of the human body in which the capsule endoscope 10 is placed and generates second data indicating the detected movement of the human body. For example, the second movement sensor 2000 is at least one of an acceleration sensor, a speed sensor, a magnetic sensor, and an angular velocity sensor. Therefore, the second movement sensor 2000 can acquire at least one of acceleration, speed, angular velocity, and magnetism data. The second movement sensor 2000 outputs the second data to the second analyzer 201.

The second analyzer 201 analyzes the second data and generates a second analysis result. The second analyzer 201 further generates instruction data on the basis of the second analysis result. The second analyzer 201 is a processor such as a CPU or a DSP, or hardware such as an ASIC or an FPGA. The second analyzer 201 outputs the second analysis result and the instruction data to the first wireless transmitter 202.

For example, when the second data is acceleration data or angular velocity data, the second analyzer 201 compares the second data with a predetermined threshold value. When the second data is speed data or magnetic data, the second analyzer 201 compares the amount of change of the second data at a plurality of times with the predetermined threshold value. A second comparison result is a result of the above comparison. The second analyzer 201 determines whether the human body is moving on the basis of the second analysis result. When it is determined that the human body is stationary, the second analyzer 201 generates instruction data to designate a first analysis result. When it is determined that the human body is moving, the second analyzer 201 generates the instruction data to designate the second analysis result.

For example, the instruction data contains a value corresponding to any one of the first analysis result and the second analysis result. For example, the instruction data contains any one of 0 and 1. 0 corresponds to the first analysis result and 1 corresponds to the second analysis result.

The first wireless transmitter 202 transmits the second analysis result and the instruction data to the capsule endoscope 10. The first wireless transmitter 202 is a wireless communication circuit.

The second movement sensor 2000 generates second data at a third period. The second data is input to the second analyzer 201 at the third period. The second analyzer 201 generates a second analysis result at the third period. The second analysis result is input to the first wireless transmitter 202 at the third period. The first wireless transmitter 202 transmits the second analysis result at a predetermined transmission period. For example, the transmission period in the first wireless transmitter 202 is equal to or longer than the third period. That is, an interval at which the second analysis result is transmitted is equal to or shorter than an interval at which the second analysis result is generated. In other words, the second analysis result is transmitted at a frequency equal to or lower than a generation frequency of the second analysis result.

For example, the functions of the second analyzer 201 can be realized as software functions by using a computer of the wireless communication device 20 reading and executing a program containing commands for defining an operation of the second analyzer 201. The implementation form of such a program is the same as the implementation form of the program realizing the functions of the first analyzer 101 and the determiner 102.

The wireless communication device 20 and the data generation unit 200 may be separately provided. For example, the data generation unit 200 may include a wireless transmitter configured to transmit the second data to the wireless communication device 20. The wireless communication device 20 may include a wireless receiver configured to receive the second data from the data generation unit 200.

Figure 4:
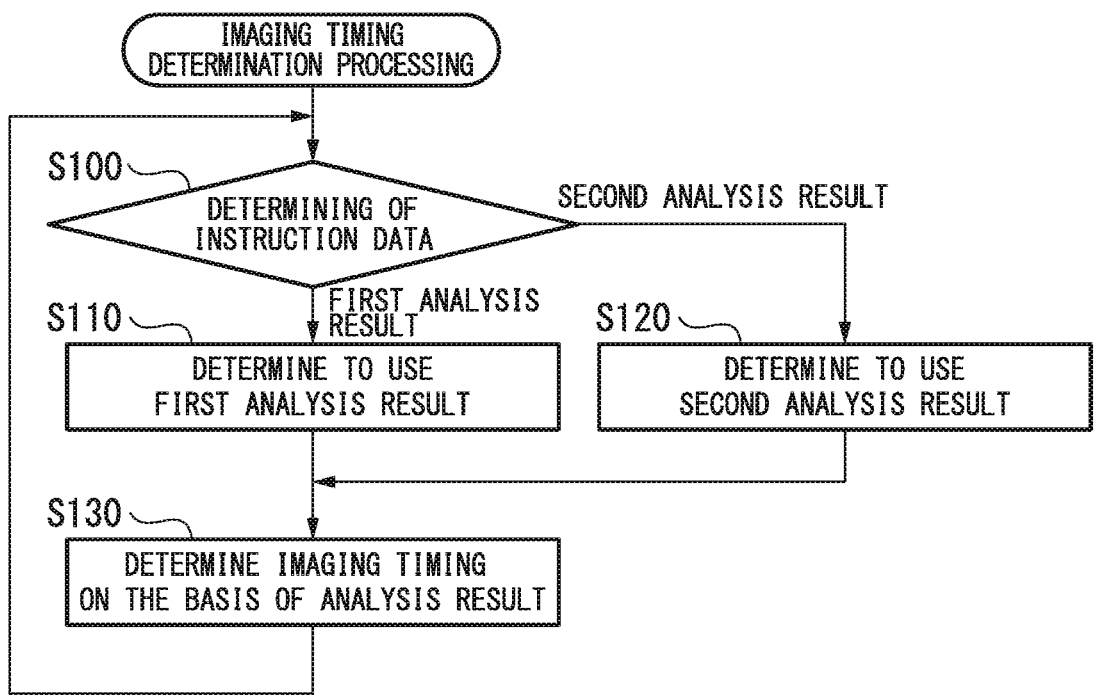
FIG. 4 is a flowchart showing an operation procedure of a capsule endoscope according to the first embodiment of the present invention.

FIG. 4 shows an operation procedure of the capsule endoscope 10 regarding the determination of an imaging timing. An operation of the capsule endoscope 10 regarding the determination of the imaging timing will be described with reference to FIG. 4.

The determiner 102 performs determination on instruction data received by the first wireless receiver 104 (Step S100). When it is determined that the instruction data designates a first analysis result, the determiner 102 determines to use the first analysis result (Step S110). When it is determined that the instruction data designates a second analysis result, the determiner 102 determines to use the second analysis result (Step S120). After Step S110 or Step S120, the determiner 102 determines an imaging timing on the basis of the first analysis result or the second analysis result (Step S130). The processes of Steps S100 to S130 are repeatedly performed.

When the human body is stationary, the instruction data designates the first analysis result. For this reason, the determiner 102 determines an imaging timing on the basis of the first analysis result. For example, when the first data or the amount of change thereof is less than a predetermined threshold value, the determiner 102 determines the imaging timing so that an imaging interval is equal to or longer than a predetermined time. In other words, the determiner 102 determines a frame rate value as a first value. When the first data or the amount of change thereof is equal to or larger than a predetermined threshold value, the determiner 102 determines an imaging timing so that the imaging interval is shorter than the predetermined time. In other words, the determiner 102 determines a frame rate value as a second value. The second value is greater than the first value. The determiner 102 can rapidly react to the movement of the capsule endoscope 10 and determine an imaging timing by using the first analysis result.

When the human body is moving, the instruction data designates the second analysis result. For this reason, the determiner 102 determines an imaging timing on the basis of the second analysis result. For example, the determiner 102 determines that the human body is moving in accordance with the second analysis result and determines a frame rate value as a third value. For example, the third value is greater than the first value and less than the second value. When the human body is moving, it is difficult to detect the movement of the capsule endoscope 10 only from the first analysis result. Power consumption is wasteful in the case in which the frame rate becomes high even when the capsule endoscope 10 is not moving with respect to the human body. For this reason, the determiner 102 can determine an imaging timing at which power consumption is reduced by using the second analysis result.

A method for determining a frame rate by using the determiner 102 is not limited to the above example. For example, any one of three or more frame rates may be set in the imager 103 on the basis of the first analysis result.

The determiner 102 may select an analysis result to be used on the basis of the first analysis result and the second analysis result. For example, the determiner 102 determines whether the human body is moving on the basis of the second analysis result. When it is determined that the human body is stationary, the determiner 102 determines to use the first analysis result. When it is determined that the human body is moving, the determiner 102 determines to use the second analysis result. For this reason, the second analyzer 201 need not generate instruction data. The first wireless transmitter 202 need not transmit instruction data. The first wireless receiver 104 need not receive instruction data.

The second analysis result and the instruction data may be configured as one piece of data. Therefore, the first wireless transmitter 202 may transmit data containing the second analysis result and the instruction data and the first wireless receiver 104 may receive data containing the second analysis result and the instruction data.

The capsule endoscope system of each aspect of the present invention need not have a component corresponding to the data generation unit 200.

As described above, the capsule endoscope system 1 includes the capsule endoscope 10 and the wireless communication device 20. The capsule endoscope 10 includes the first movement sensor 100, the first analyzer 101, the determiner 102, the imager 103, and the first wireless receiver 104. The first movement sensor 100 detects the movement of the capsule endoscope 10 and generates first data indicating the detected movement of the capsule endoscope 10. The first analyzer 101 analyzes the first data and generates a first analysis result. The determiner 102 determines an imaging timing. The imager 103 performs imaging at the imaging timing determined by the determiner 102 and acquires an image. The first wireless receiver 104 receives a second analysis result from the wireless communication device 20. The wireless communication device 20 includes the second analyzer 201 and the first wireless transmitter 202. The second analyzer 201 analyzes second data and generates the second analysis result. The first wireless transmitter 202 transmits the second analysis result to the capsule endoscope 10. The first analyzer 101 outputs the first analysis result at a first period equal to or shorter than a reception period at which the first wireless receiver 104 receives the second analysis result. The first analysis result and the second analysis result are input to the determiner 102. The determiner 102 determines an imaging timing at a second period equal to or shorter the reception period on the basis of any one of the first analysis result and the second analysis result.

The second analyzer 201 further generates instruction data to designate any one of the first analysis result and the second analysis result on the basis of the second analysis result. The first wireless transmitter 202 further transmits the instruction data to the capsule endoscope 10. The first wireless receiver 104 further receives the instruction data from the wireless communication device 20. The instruction data is input to the determiner 102. The determiner 102 selects any one of the first analysis result and the second analysis result on the basis of the instruction data.

The wireless communication device 20 further includes the second movement sensor 2000 detects the movement of the human body in which the capsule endoscope 10 is placed and generates the second data indicating the detected movement of the human body.

In the first embodiment, the determiner 102 determines an imaging timing at the second period equal to or shorter the reception period on the basis of any one of the first analysis result and the second analysis result. For this reason, the capsule endoscope system 1 can achieve both a high-speed response to the movement of the capsule endoscope 10 and determination of a frame rate based on a plurality of analyses.

An analysis regarding the movement of the human body is performed by the wireless communication device 20. For this reason, power consumption of the capsule endoscope 10 is reduced and a circuit size of the capsule endoscope 10 is decreased. As a result, a size of the capsule endoscope 10 is reduced.

Second Embodiment

Figure 5:
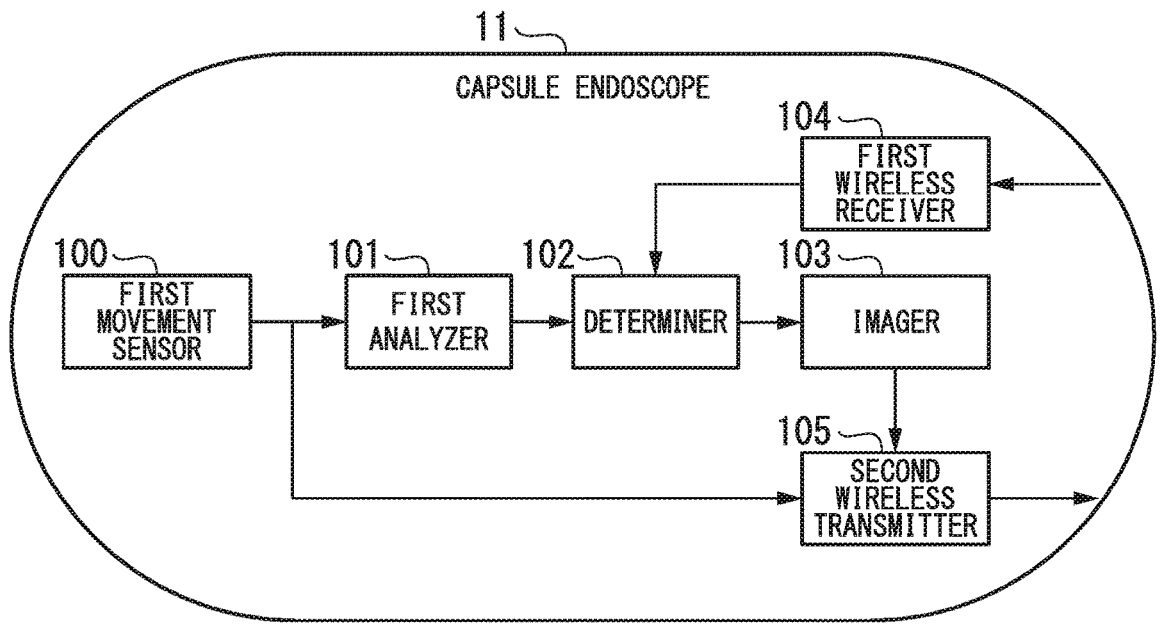
FIG. 5 is a block diagram showing a configuration of a capsule endoscope according to a second embodiment of the present invention.
Figure 6:
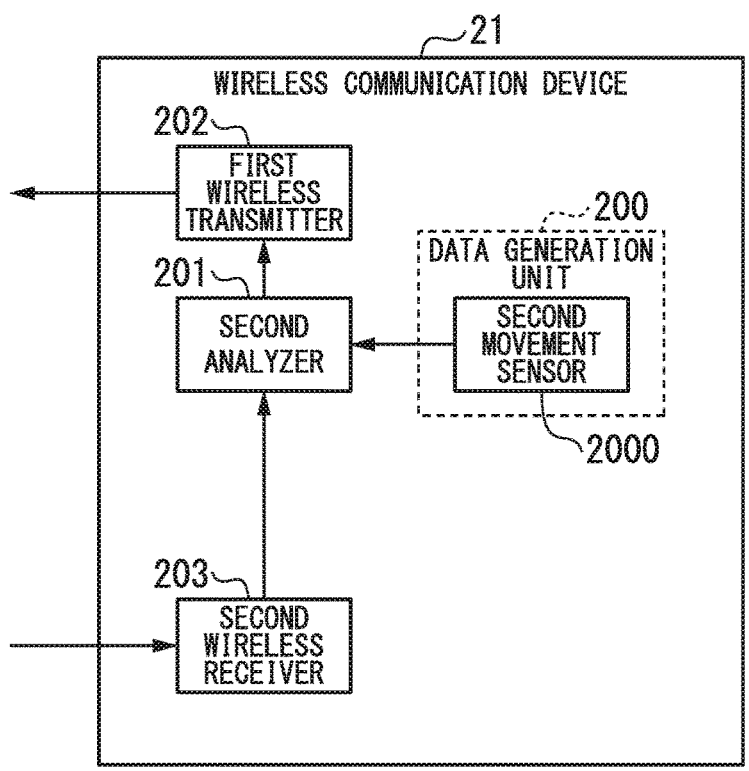
FIG. 6 is a block diagram showing a configuration of a wireless communication device according to the second embodiment of the present invention.

In a second embodiment of the present invention, the capsule endoscope 10 in the first embodiment is changed to a capsule endoscope 11 shown in FIG. 5 and the wireless communication device 20 in the first embodiment is changed to a wireless communication device 21 shown in FIG. 6.

FIG. 5 shows a configuration of the capsule endoscope 11. As shown in FIG. 5, the capsule endoscope 11 includes a first movement sensor 100, a first analyzer 101, a determiner 102, an imager 103, a first wireless receiver 104, and a second wireless transmitter 105. With regard to the configuration shown in FIG. 5, differences from the configuration shown in FIG. 2 will be described.

The first movement sensor 100 outputs the first data to the first analyzer 101 and the second wireless transmitter 105. The second wireless transmitter 105 transmits at least one of the first data generated by the first movement sensor 100 and the image generated by the imager 103 to the wireless communication device 21. The second wireless transmitter 105 is a wireless communication circuit. A single wireless communication unit including the first wireless receiver 104 and the second wireless transmitter 105 may be provided.

With regard to matters other than the above description, the configuration shown in FIG. 5 is the same as the configuration shown in FIG. 2.

FIG. 6 shows a configuration of the wireless communication device 21. As shown in FIG. 6, the wireless communication device 21 includes a data generation unit 200, a second analyzer 201, a first wireless transmitter 202, and a second wireless receiver 203. With regard to the configuration shown in FIG. 6, differences from the configuration shown in FIG. 3 will be described.

The second wireless receiver 203 receives at least one of the first data and the image from the capsule endoscope 11. The second wireless receiver 203 outputs at least one of the first data and the image to the second analyzer 201. The second wireless receiver 203 is a wireless communication circuit. A single wireless communication unit including the first wireless transmitter 202 and the second wireless receiver 203 may be provided.

The second analyzer 201 analyzes the second data output from the second movement sensor 2000 and the first data and generates a second analysis result. Alternatively, the second analyzer 201 analyzes the image and generates a second analysis result. The second analyzer 201 further generates instruction data on the basis of the second analysis result. The second analyzer 201 performs an analysis by using a different calculation method from a calculation method for an analysis by the first analyzer 101.

The second analyzer 201 calculates a difference between the first data and the second data in the analysis of the second data from the second movement sensor 2000 and the first data. Thus, the second analyzer 201 can detect a relative movement of the capsule endoscope 11 with respect to the human body. The second analyzer 201 compares the calculated difference with a predetermined threshold value. The second analysis result is a result of such comparison.

The second analyzer 201 can detect the relative movement of the capsule endoscope 11 with respect to the human body by analyzing the image. For example, the second analyzer 201 calculates a difference between two consecutive frames. When the movement of the capsule endoscope 11 with respect to the human body is large, the difference between the images is equal to or larger than a predetermined threshold value. When the movement of the capsule endoscope 11 with respect to the human body is small, a difference between the images is less than the predetermined threshold value. The second analyzer 201 compares the calculated difference with the predetermined threshold value. The second analysis result is a result of such comparison. The second data analyzed by the second analyzer 201 is the image.

The second analyzer 201 determines whether the human body is moving on the basis of the second data from the second movement sensor 2000. When it is determined that the human body is stationary, the second analyzer 201 generates instruction data to designate a first analysis result. When it is determined that the human body is moving, the second analyzer 201 generates instruction data to designate a second analysis result.

With regard to matters other than the above description, the configuration shown in FIG. 6 is the same as the configuration shown in FIG. 3.

The second wireless transmitter 105 may transmit only the first data between the first data and the image, and the second wireless receiver 203 may receive only the first data between the first data and the image. The second analyzer 201 may analyze only the second data from the second movement sensor 2000 and the first data.

The second wireless transmitter 105 may transmit only the image between the first data and the image, and the second wireless receiver 203 may receive only the image between the first data and the image. The second analyzer 201 may analyze only the image. Therefore, the wireless communication device 21 need not include the data generation unit 200. The second analyzer 201 may analyze only the image.

When the second wireless transmitter 105 transmits only the first data, a transmission period in the second wireless transmitter 105 is equal to or longer than the first period at which the first movement sensor 100 generates the first data. That is, an interval at which the first data is transmitted is equal to or longer than an interval at which the first data is generated. In other words, the first data is transmitted at a frequency equal to or lower than the generation frequency of the first data. For example, a transmission period in the first wireless transmitter 202 is the same as the transmission period in the second wireless transmitter 105.

When the second wireless transmitter 105 transmits at least the image, the transmission period in the second wireless transmitter 105 is equal to or longer than the imaging period in the imager 103. That is, an interval at which the image is transmitted is equal to or longer than the imaging interval. In other words, the image is transmitted at a frequency equal to or lower than the imaging frequency. For example, the transmission period in the first wireless transmitter 202 is the same as the transmission period in the second wireless transmitter 105.

An operation of the capsule endoscope 11 regarding the determination of an imaging timing is the same as the operation described with reference to FIG. 4.

When the instruction data designates the second analysis result, the determiner 102 determines an imaging timing on the basis of the second analysis result. For example, when the difference is less than a predetermined threshold value, the determiner 102 determines the imaging timing so that the imaging interval is equal to or longer than a predetermined time. In other words, the determiner 102 determines a frame rate as a first value. When the difference is equal to or larger than the predetermined threshold value, the determiner 102 determines the imaging timing so that the imaging interval is shorter than the predetermined time. In other words, the determiner 102 determines a frame rate value as a second value. The second value is larger than the first value.

When the human body is moving, it is difficult to detect the movement of the capsule endoscope 11 only from the first analysis result. For this reason, the determiner 102 can accurately respond to the movement of the capsule endoscope 11 to determine an imaging timing by using the second analysis result.

When the instruction data designates the first analysis result, the determiner 102 determines an imaging timing on the basis of the first analysis result. A method for determining the imaging timing based on the first analysis result is the same as the method described in the first embodiment.

Figure 7:
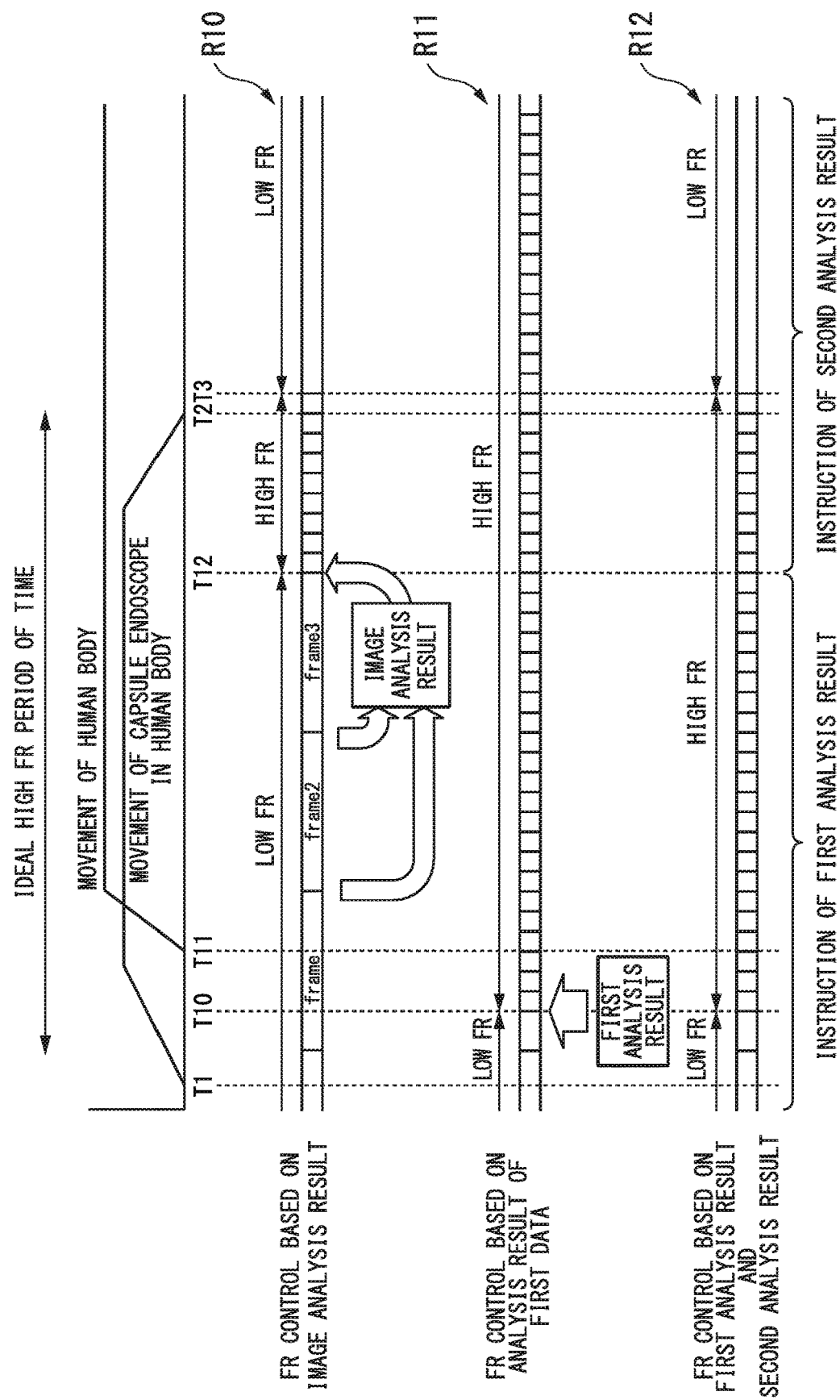
FIG. 7 is a timing chart showing a method for controlling a frame rate according to the second embodiment of the present invention.

FIG. 7 shows an example of a method for controlling a frame rate. Time advances in the right direction in FIG. 7. "Low FR" indicates that a frame rate is low. "High FR" indicates that a frame rate is high. An "ideal high FR period of time" is an ideal period of time in which a high frame rate is set in the imager 103. In FIG. 7, time for communication between the capsule endoscope 11 and the wireless communication device 21 is not taken into consideration for simplicity of explanation.

The capsule endoscope 11 is stationary before a timing T1. At the timing T1, a low frame rate has been set in the imager 103. At the timing T1, the capsule endoscope 11 starts to move. After a movement speed gradually increases, the capsule endoscope 11 moves at a constant speed. After that, the movement speed gradually decreases. At a timing T2, the capsule endoscope 11 finishes the movement thereof. An "ideal high FR period of time" is a period of time from a timing immediately after the timing T1 at which the capsule endoscope 11 starts to move to a timing immediately before the timing T2 at which the capsule endoscope 11 finishes the movement thereof.

In FIG. 7, a control result R10 of a frame rate based on an analysis result of an image is shown. The control result R10 of the frame rate is a control result when it is assumed that the second analyzer 201 analyzes an image and the determiner 102 determines a frame rate based only on the analysis result of the image. For example, in the analysis of an image, a difference between images of two consecutive frames is calculated.

When a low frame rate is set in the imager 103, an acquisition frequency of an image is low. After the timing T1, a difference calculated by using an image acquired when a movement speed of the capsule endoscope 11 is small is less than a predetermined threshold value. For this reason, it is determined that the frame rate is set to a low value. After the timing T1, a difference calculated by using an image acquired when a movement speed of the capsule endoscope 11 is high is equal to or larger than a predetermined threshold value. For this reason, it is determined that the frame rate is set to a high value. At a timing T12 apart from the timing T1, the frame rate is changed to a high value. When a high frame rate is set in the imager 103, an acquisition frequency of an image is high.

After the timing T1, the capsule endoscope 11 stops the movement at the timing T2. When a movement speed of the capsule endoscope 11 is low, an image difference is less than a predetermined threshold value. For this reason, it is determined that the frame rate is set to a low value. After the timing T2, the frame rate is changed to a low value at a timing T3.

When the frame rate is controlled based only on the analysis result of the image, the timing T12 at which the frame rate is changed from the low value to the high value is far away from the timing T1 at which the capsule endoscope 11 starts to move. When communication time between the capsule endoscope 11 and the wireless communication device 21 is considered, a timing at which the frame rate is changed from the low value to the high value is later than the timing T12. Therefore, when the determiner 102 determines a frame rate based only on the analysis result of the image, it is difficult for the capsule endoscope 11 to switch the frame rate at a high speed.

In FIG. 7, a control result R11 of a frame rate based on the analysis result of the first data is shown. The control result R11 of the frame rate is a control result when it is assumed that the determiner 102 determines the frame rate based only on the analysis result of the first data. For example, the first data generated by the first movement sensor 100 is acceleration data.

Immediately after the capsule endoscope 11 starts to move, acceleration becomes equal to or higher than a predetermined threshold value due to the movement. For this reason, it is determined that the frame rate is set to the high value. A period at which the determiner 102 acquires the first analysis result is relatively short. For this reason, at a timing T10 close to the timing T1, the frame rate is changed to a high value.

After the timing T10, the human body starts to move at a timing T11. After the timing T11, the capsule endoscope 11 stops moving at the timing T2. However, since the human body continues to move, acceleration is equal to or higher than a predetermined threshold value. As a result, after the timing T10, the frame rate is maintained at the high value.

When the frame rate is controlled based only on the analysis result of the first data, the frame rate is maintained at the high value due to the movement of the human body after the capsule endoscope 11 stops moving For this reason, it is difficult for the capsule endoscope 11 to accurately control the frame rate.

As described above, when the frame rate is controlled based only on the analysis result of the image or only on the analysis result of the first data at all times, it is difficult to accurately control the frame rate.

In FIG. 7, a control result R12 of a frame rate based on the first analysis result and the second analysis result is shown. The control result R12 of the frame rate is a control result when the determiner 102 selects one of the first analysis result and the second analysis result, and determines a frame rate on the basis of the selection result. For example, the second data generated by the second movement sensor 2000 is acceleration data.

When a low frame rate is set in the imager 103, an acquisition frequency of an image is low. After the timing T1, a difference calculated by using an image acquired when a movement speed of the capsule endoscope 11 is small is less than a predetermined threshold value. When the frame rate is low, it is desirable that the frame rate be set to a high value in immediate response to the movement of the capsule endoscope 11. For this reason, the second analyzer 201 generates instruction data to designate a first analysis result.

After the timing T1, a difference calculated by using an image acquired when a movement speed of the capsule endoscope 11 is high is equal to or larger than a predetermined threshold value. When the capsule endoscope 11 is moving, it is desirable that the frame rate be controlled on the basis of the movement of the capsule endoscope 11 itself regardless of the movement of the human body. For this reason, at the timing T12, the second analyzer 201 generates instruction data to designate a second analysis result.

After the timing T12, the capsule endoscope 11 stops moving at the timing T2. When a movement speed of the capsule endoscope 11 is small, an image difference is less than a predetermined threshold value. On the other hand, acceleration indicated by the second data is equal to or higher than a predetermined value. When the human body is moving, it is desirable that the frame rate be controlled on the basis of the movement of the capsule endoscope 11 itself. For this reason, the second analyzer 201 generates instruction data to designate a second analysis result.

After the timing T1, the determiner 102 selects a first analysis result on the basis of the instruction data to designate the first analysis result. Acceleration indicated by the first data is less than a predetermined threshold value until the timing T10. For this reason, the frame rate is maintained at the low value. At the timing T10, the acceleration indicated by the first data is equal to or higher than a predetermined threshold value. For this reason, the frame rate is changed to a high value. After the timing T12, the determiner 102 selects the second analysis result on the basis of the instruction data to designate the second analysis result. Until the timing T2, an image difference is equal to or larger than a predetermined threshold value. For this reason, the frame rate is maintained at the high value. After the timing T2, the determiner 102 selects the second analysis result on the basis of the instruction data to designate the second analysis result. After the timing T2, since the human body continues to move, the accelerator indicated by the second data is equal to or higher than a predetermined threshold value. On the other hand, an image difference is less than a predetermined threshold value. For this reason, the frame rate is changed to a low value.

When the second analyzer 201 analyzes only an image, the determiner 102 may detect the movement of the human body on the basis of the first analysis result and the second analysis result. For example, when the first data or the amount of change thereof is less than a predetermined threshold value, the determiner 102 can determine that the human body is stationary. For this reason, the determiner 102 determines an imaging timing on the basis of the first analysis result. When an image difference is less than a predetermined threshold value and the first data or the amount of change thereof is equal to or larger than the predetermined threshold value, the determiner 102 can determine that the human body is moving. For this reason, the determiner 102 determines an imaging timing on the basis of the second analysis result. When an image difference is equal to or larger than the predetermined threshold value and the first data or the amount of change thereof is equal to or larger than the predetermined threshold value, the human body is likely to be moving. For this reason, the determiner 102 determines an imaging timing on the basis of the second analysis result. Therefore, when the second analyzer 201 analyzes only an image, instruction data is unnecessary.

A method for determining a frame rate by using the determiner 102 is not limited to the above example. For example, any one of three or more frame rates may be set in the imager 103 on the basis of the first analysis result or the second analysis result.

As described above, the capsule endoscope 11 includes the second wireless transmitter 105 configured to transmit first data to the wireless communication device 21. The wireless communication device 21 includes the second wireless receiver 203 configured to receive first data from the capsule endoscope 11. The second analyzer 201 analyzes first data and second data.

As described above, the capsule endoscope 11 includes the second wireless transmitter 105 configured to transmit an image to the wireless communication device 21. The wireless communication device 21 includes the second wireless receiver 203 configured to receive an image from the capsule endoscope 11. The second analyzer 201 analyzes an image. An image may be second data.

In the second embodiment, like in the first embodiment, the capsule endoscope system 1 can achieve both a rapid response to the movement of the capsule endoscope 11 and determination of a frame rate based on a plurality of analyses.

The second analyzer 201 can perform a more complex analysis than the first analysis performed by the first analyzer 101. The second analyzer 201 can analyze the second data from the second movement sensor 2000 and the first data, or analyze the image to accurately detect the movement of the capsule endoscope 11. As a result, the determiner 102 can determine an imaging timing on the basis of accurate movement of the capsule endoscope 11 with respect to the human body.

Third Embodiment

Figure 8:
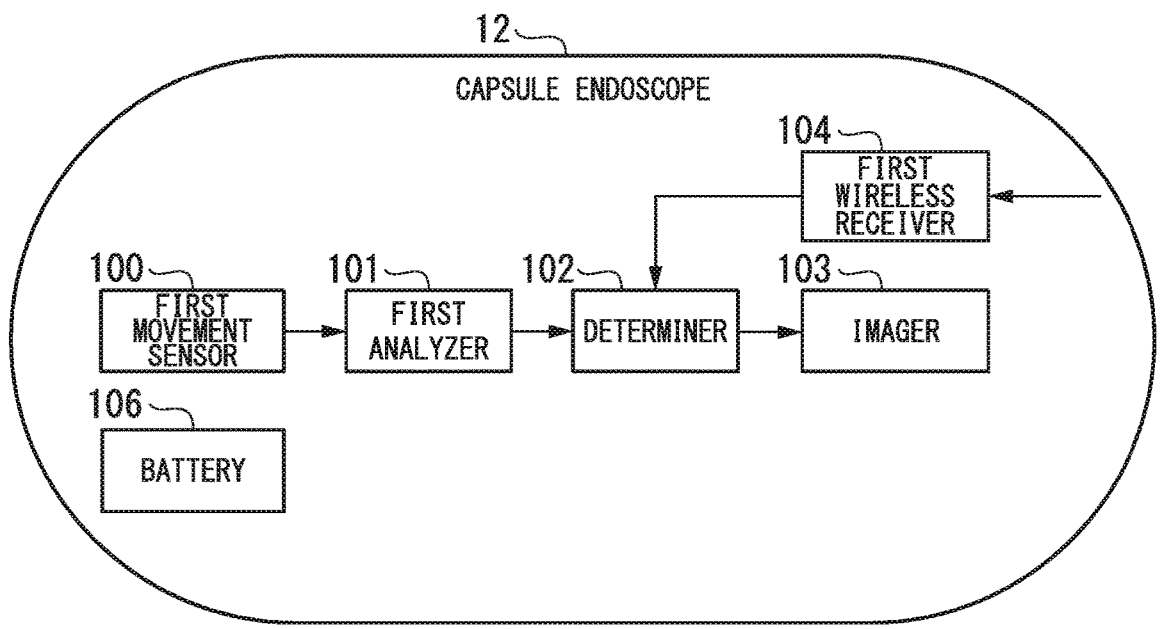
FIG. 8 is a block diagram showing a configuration of a capsule endoscope according to a third embodiment of the present invention.
Figure 9:
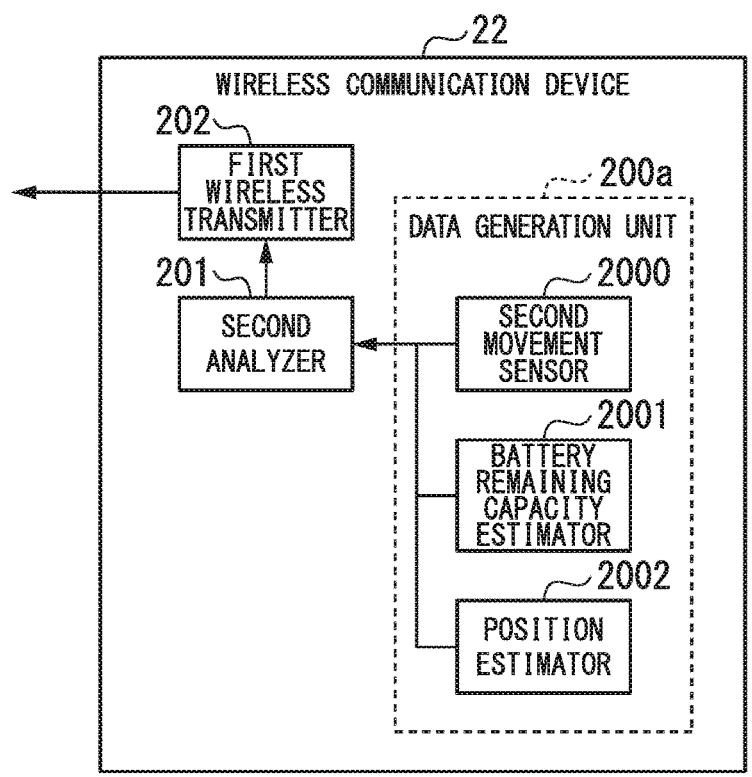
FIG. 9 is a block diagram showing a configuration of a wireless communication device according to the third embodiment of the present invention.

In a third embodiment of the present invention, the capsule endoscope 10 according to the first embodiment is changed to a capsule endoscope 12 shown in FIG. 8 and the wireless communication device 20 according to the first embodiment is changed to a wireless communication device 22 shown in FIG. 9.

FIG. 8 shows a configuration of the capsule endoscope 12. As shown in FIG. 8, the capsule endoscope 12 includes a first movement sensor 100, a first analyzer 101, a determiner 102, an imager 103, a first wireless receiver 104, and a battery 106. In the configuration shown in FIG. 8, differences from the configuration shown in FIG. 2 will be described.

The battery 106 supplies electric power to the first movement sensor 100, the first analyzer 101, the determiner 102, the imager 103, and the first wireless receiver 104. The capsule endoscope 10 according to the first embodiment may include the battery 106. Description of the battery 106 in the first embodiment is unnecessary. For this reason, the battery 106 is not shown in FIG. 2.

With regard to matters other than the above description, the configuration shown in FIG. 8 is the same as the configuration shown in FIG. 2.

FIG. 9 shows the configuration of the wireless communication device 22. As shown in FIG. 9, the wireless communication device 22 includes a data generation unit 200*a*, a second analyzer 201, and a first wireless transmitter 202. With regard to the configuration shown in FIG. 9, differences from the configuration shown in FIG. 3 will be described.

The data generation unit 200*a* includes a second movement sensor 2000, a battery remaining capacity estimator 2001, and a position estimator 2002. The second movement sensor 2000 is the same as the second movement sensor 2000 in FIG. 2. The battery remaining capacity estimator 2001 estimates a remaining capacity of the battery 106 and generates second data indicating the estimated remaining capacity. The battery remaining capacity estimator 2001 outputs the second data to the second analyzer 201. The position estimator 2002 estimates a position (a specific organ or the like) of the capsule endoscope 12 and generates the second data indicating the estimated position. The position estimator 2002 outputs the second data to the second analyzer 201.

The battery remaining capacity estimator 2001 estimates a remaining capacity of the battery 106 by using the following method. For example, the battery remaining capacity estimator 2001 estimates a remaining capacity of the battery 106 on the basis of time elapsing after the capsule endoscope 12 starts to operate. When the capsule endoscope 12 includes a second wireless transmitter 105 and the wireless communication device 22 includes a second wireless receiver 203, the battery remaining capacity estimator 2001 may estimate a remaining capacity of the battery 106 on the basis of the number of images captured by the imager 103. The battery remaining capacity estimator 2001 may receive information indicating a remaining capacity of the battery 106 from the capsule endoscope 12.

The position estimator 2002 estimates a position of the capsule endoscope 12 by using the following method. When the capsule endoscope 12 includes the second wireless transmitter 105 and the wireless communication device 22 includes the second wireless receiver 203, the position estimator 2002 detects a position of the capsule endoscope 12 by analyzing an image received from the capsule endoscope 12. The position estimator 2002 may detect a position of the capsule endoscope 12 by measuring an intensity of radio waves from the capsule endoscope 12. When a magnet is placed in the capsule endoscope 12, the position estimator 2002 may detect a position of the capsule endoscope 12 by measuring an intensity of magnetism from the capsule endoscope 12.

The second analyzer 201 analyzes second data from each of the second movement sensor 2000, the battery remaining capacity estimator 2001, and the position estimator 2002. In the analysis based on the second data from each of the battery remaining capacity estimator 2001 and the position estimator 2002, the second analyzer 201 performs analysis by using a different calculation method from the calculation method of the analysis used by the first analyzer 101.

The second analyzer 201 generates a second analysis result on the basis of the second data acquired by the second movement sensor 2000. The second analysis result is an analysis result regarding the movement of the human body. The analysis result regarding the movement of the human body is the same as the second analysis result in the first embodiment.

The second analyzer 201 determines whether a remaining capacity of the battery 106 is sufficient on the basis of the second data from the battery remaining capacity estimator 2001. The second analyzer 201 generates a second analysis result indicating whether the remaining capacity of the battery 106 is sufficient. The second analyzer 201 determines whether imaging in an area to be inspected has been completed on the basis of the second data from the position estimator 2002. The second analyzer 201 generates a second analysis result indicating whether the imaging in the area to be inspected has been completed.

The second analyzer 201 further generates instruction data on the basis of the second analysis result. The second analyzer 201 determines whether the human body is moving on the basis of an analysis result regarding the movement of the human body. When it is determined that the human body is moving, the second analyzer 201 generates instruction data to designate the second analysis result. When a remaining capacity of the battery 106 is not sufficient, the second analyzer 201 generates instruction data to designate the second analysis result. When the imaging in the area to be inspected has been completed, the second analyzer 201 generates instruction data to designate the second analysis result. When neither of the above conditions is satisfied, the second analyzer 201 generates instruction data to designate the first analysis result.

With regard to matters other than the above description, the configuration shown in FIG. 9 is the same as the configuration shown in FIG. 3.

An operation of the capsule endoscope 12 regarding the determination of an imaging timing is the same as the operation shown in FIG. 4.

When the instruction data designates the second analysis result, the determiner 102 refers to an analysis result regarding the movement of the human body in the second analysis result. When the human body is moving, the determiner 102 determines a value of a frame rate as a third value. For example, the third value is larger than a first value and is smaller than a second value. The first value and the second value are frame rates determined on the basis of the first analysis result. When the human body is moving, it is difficult to detect the movement of the capsule endoscope 12 from only the first analysis result. When a frame rate is high despite the fact that the capsule endoscope 12 is not moving with respect to the human body, power consumption is wasteful. For this reason, the determiner 102 can determine an imaging timing at which power consumption is reduced by using the second analysis result.

The determiner 102 further refers to an analysis result regarding a remaining capacity of the battery 106. When a remaining capacity of the battery 106 is not sufficient, the determiner 102 determines a frame rate as a fourth value. The fourth value is smaller than the second value. The fourth value may be the same as the first value or the third value. When a remaining capacity of the battery 106 is not sufficient, power consumption of the capsule endoscope 12 is reduced by setting a low frame rate in the imager 103. As a result, the capsule endoscope 12 can continue imaging.

The determiner 102 further refers to an analysis result regarding a position of the capsule endoscope 12. When imaging in an area to be inspected has been completed, the determiner 102 determines a frame rate as a fifth value. The fifth value is smaller than the second value. The fifth value may be the same as any one of the first value, the third value, and the fourth value. When imaging in an area to be inspected has been completed, a low frame rate is set in the imager 103 so that power consumption of the capsule endoscope 12 is reduced. As a result, when inspection is necessary in another area, the capsule endoscope 12 can continue imaging.

When instruction data designates a first analysis result, the determiner 102 determines an imaging timing on the basis of the first analysis result. A method for determining an imaging timing based on the first analysis result is the same as the method described in the first embodiment.

A method for determining a frame rate by using the determiner 102 is not limited to the above example.

The capsule endoscope 12 may include the second wireless transmitter 105 and the wireless communication device 22 may include the second wireless receiver 203. The battery 106 may supply electric power to the second wireless transmitter 105. The second analyzer 201 may analyze the second data from the second movement sensor 2000 and the first data to detect a relative movement of the capsule endoscope 12 with respect to the human body. Alternatively, the second analyzer 201 may analyze the image to detect a relative movement of the capsule endoscope 12 with respect to the human body.

The capsule endoscope system according to each aspect of the present invention need not have a configuration corresponding to at least one of the second movement sensor 2000, the battery remaining capacity estimator 2001, and the position estimator 2002.

As described above, the capsule endoscope 12 includes the battery 106 configured to supply electric power to the first movement sensor 100, the first analyzer 101, the determiner 102, the imager 103, and the first wireless receiver 104. The wireless communication device 22 includes the battery remaining capacity estimator 2001 (estimator) configured to estimate a remaining capacity of the battery 106 and generate second data indicating the estimated remaining capacity.

The wireless communication device 22 includes the position estimator 2002 (estimator) configured to estimate a position of the capsule endoscope 12 and generate second data indicating the estimated position.

In the third embodiment, like in the first embodiment, the capsule endoscope system 1 can achieve both a rapid response to the movement of the capsule endoscope 12 and determination of a frame rate based on a plurality of analyses.

The second analyzer 201 can perform a more complex analysis than the first analysis performed by the first analyzer 101. The second analyzer 201 can analyze the second data from the battery remaining capacity estimator 2001 to determine whether a remaining capacity of the battery 106 is sufficient. As a result, the determiner 102 can determine an imaging timing on the basis of the remaining capacity of the battery 106.

The second analyzer 201 can analyze the second data from the position estimator 2002 to determine whether imaging in the area to be inspected has been completed. As a result, the determiner 102 can determine an imaging timing on the basis of a position of the capsule endoscope 12.

Fourth Embodiment

Figure 10:
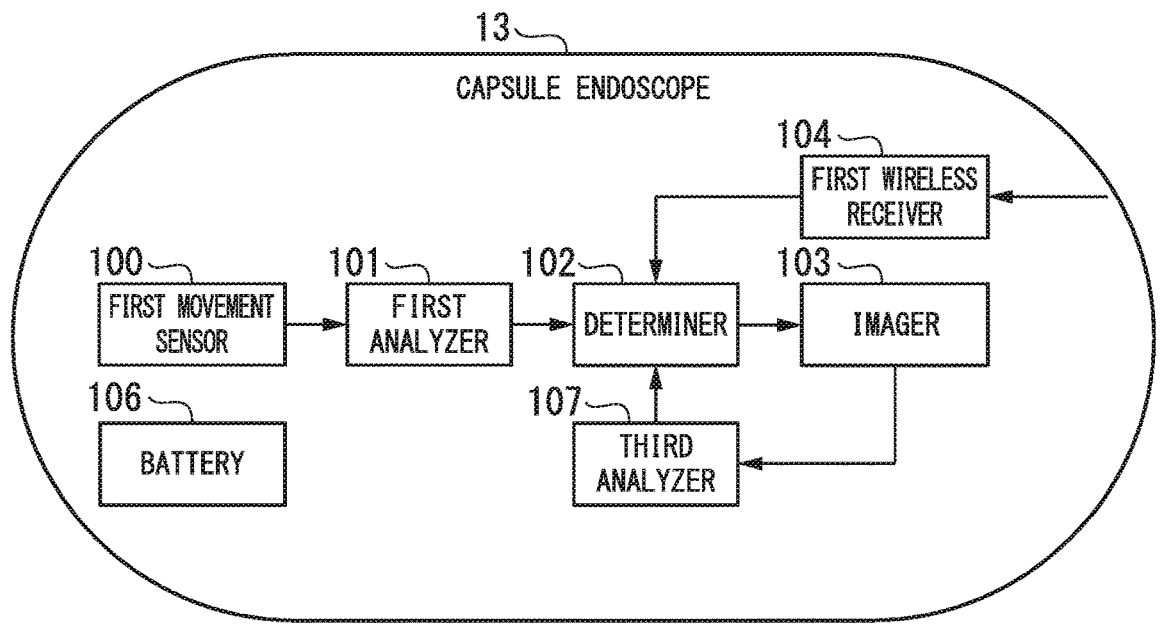
FIG. 10 is a block diagram showing a configuration of a capsule endoscope according to a fourth embodiment of the present invention.

In a fourth embodiment of the present invention, the capsule endoscope 12 in the third embodiment is changed to a capsule endoscope 13 shown in FIG. 10.

FIG. 10 shows a configuration of the capsule endoscope 13. As shown in FIG. 10, the capsule endoscope 13 includes a first movement sensor 100, a first analyzer 101, a determiner 102, an imager 103, a first wireless receiver 104, a battery 106, and a third analyzer 107. With regard to the configuration shown in FIG. 10, differences from the configuration shown in FIG. 8 will be described.

The third analyzer 107 analyzes an image acquired by the imager 103 and generates a third analysis result. The third analyzer 107 is a processor such as a CPU or a DSP, or hardware such as an ASIC or an FPGA. Single hardware including two or more of the first analyzer 101, the determiner 102, and the third analyzer 107 may be configured. The third analyzer 107 outputs the third analysis result to the determiner 102.

The third analyzer 107 can analyze the image to detect a relative movement of the capsule endoscope 13 with respect to the human body. For example, the third analyzer 107 calculates an image difference between two consecutive frames. When the movement of the capsule endoscope 13 with respect to the human body is large, the image difference is equal to or larger than a predetermined threshold value. When the movement of the capsule endoscope 13 with respect to the human body is small, the image difference is less than the predetermined threshold value. The third analyzer 107 compares the calculated difference with the predetermined threshold value. The third analysis result is a result of this comparison.

Analysis of the image by the third analyzer 107 is different from analysis of the image by the second analyzer 201 in the second embodiment. The amount of calculation of an image analysis by the third analyzer 107 is smaller than the amount of calculation of image analysis by the second analyzer 201 in the second embodiment. For example, the third analyzer 107 analyzes only a partial area of the image. When the image is formed of image signals corresponding to red (R), green (G), and blue (B), the third analyzer 107 may analyze one of the image signals corresponding to only one color. Alternatively, the third analyzer 107 may analyze a luminance (Y) signal generated from image signals of three colors.

The determiner 102 determines an imaging timing on the basis of any one of a first analysis result, a second analysis result, and a third analysis result.

The imager 103 generates an image at an imaging period based on a set frame rate. A first period at which the first movement sensor 100 generates first data is equal to or shorter than the imaging period. The image is input to the third analyzer 107 at the imaging period. The third analyzer 107 generates the third analysis result at the imaging period. The third analysis result is input to the determiner 102 at the imaging period. The first wireless receiver 104 receives the second analysis result at a predetermined reception period. The first period is equal to or shorter than the reception period. The second analysis result is input to the determiner 102 at the reception period. The determiner 102 determines an imaging timing at the second period that is equal to or shorter than the reception period and equal to or shorter than the imaging period. For example, the first period and the second period are the same.

With regard to matters other than the above description, the configuration shown in FIG. 10 is the same as the configuration shown in FIG. 8.

In a wireless communication device 22, the second analyzer 201 performs the same analysis as the analysis in the third embodiment. The second analyzer 201 further generates instruction data on the basis of the second analysis result. The second analyzer 201 determines whether the human body is moving on the basis of an analysis result regarding the movement of the human body. When it is determined that the human body is moving, the second analyzer 201 generates instruction data to designate the third analysis result. When a remaining capacity of the battery 106 is not sufficient, the second analyzer 201 generates instruction data to designate the second analysis result. When imaging in an area to be inspected has been completed, the second analyzer 201 generates instruction data to designate the second analysis result. When neither of the above conditions is satisfied, the second analyzer 201 generates instruction data to designate the first analysis result.

Figure 11:
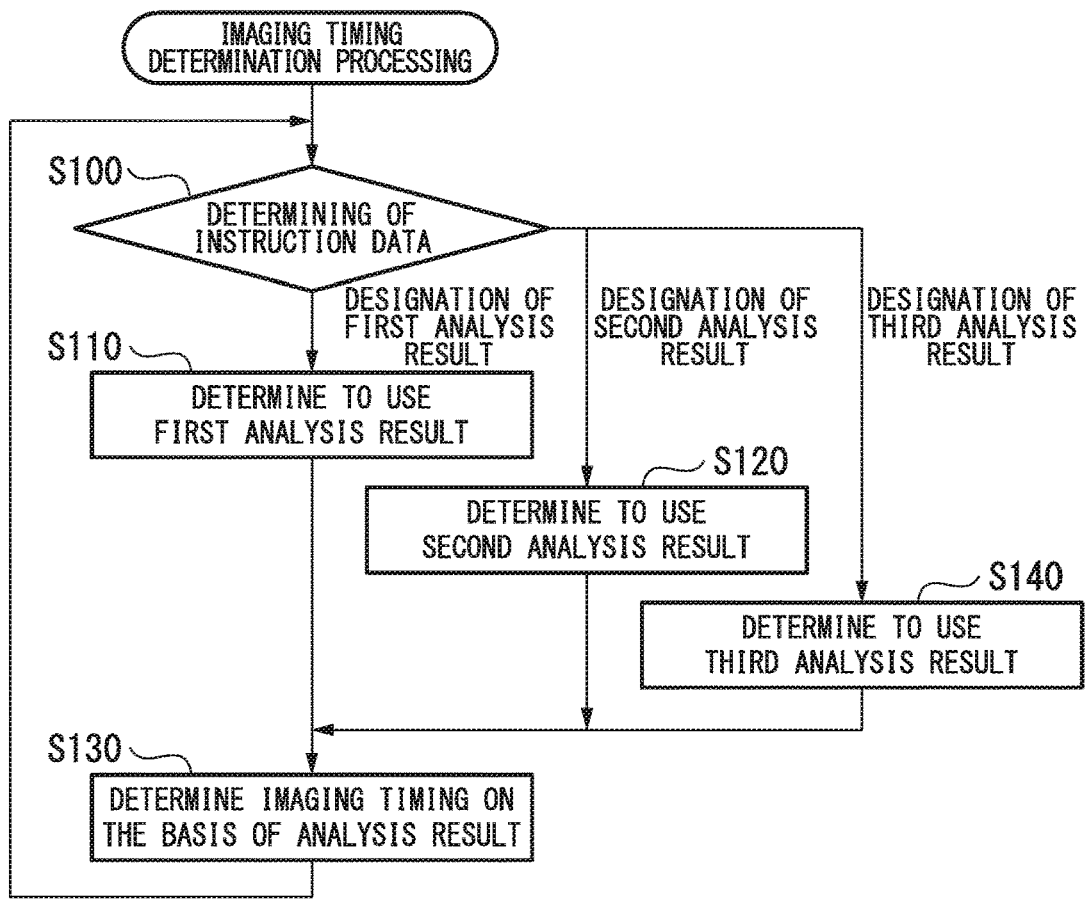
FIG. 11 is a flowchart showing an operation procedure of the capsule endoscope according to the fourth embodiment of the present invention.

FIG. 11 shows an operation procedure of the capsule endoscope 13 regarding the determination of an imaging timing. An operation of the capsule endoscope 13 regarding the determination of the imaging timing will be described with reference to FIG. 11. With regard to the operation shown in FIG. 11, differences from the operation shown in FIG. 4 will be described.

The determiner 102 determines instruction data received by the first wireless receiver 104 (Step S100). When the instruction data designates the third analysis result, the determiner 102 determines to use the third analysis result (Step S140). After any one of Step S110, Step S120, and Step S140, the determiner 102 determines an imaging timing on the basis of any one of the first analysis result, the second analysis result, and the third analysis result (Step S130).

With regard to matters other than the above description, the operation shown in FIG. 11 is the same as the operation shown in FIG. 4.

When the instruction data designates the third analysis result, the determiner 102 determines an imaging timing on the basis of the third analysis result. For example, when a difference is less than a predetermined threshold value, the determiner 102 determines an imaging timing so that an imaging interval is equal to or larger than a predetermined time. In other words, the determiner 102 determines a frame rate as a first value. When a difference is equal to or larger than a predetermined threshold value, the determiner 102 determines an imaging timing so that an imaging interval is shorter than a predetermined time. In other words, the determiner 102 determines a frame rate as a second value. The second value is larger than the first value.

When the human body is moving, it is difficult to detect the movement of the capsule endoscope 13 from only the first analysis result. For this reason, the determiner 102 can accurately react to the movement of the capsule endoscope 13 to determine an imaging timing by using the third analysis result.

When the instruction data designates the second analysis result, the determiner 102 determines an imaging timing on the basis of the second analysis result. A method for determining an imaging timing based on the second analysis result is the same as the method described in the third embodiment.

When the instruction data designates the first analysis result, the determiner 102 determines an imaging timing on the basis of the first analysis result. A method for determining an imaging timing based on the first analysis result is the same as the method described in the first embodiment.

A method for determining a frame rate by using the determiner 102 is not limited to the above example.

The capsule endoscope 13 may include a second wireless transmitter 105 and the wireless communication device 22 may include a second wireless receiver 203. The battery 106 may supply electric power to the second wireless transmitter 105. The second analyzer 201 may analyze second data from a second movement sensor 2000 and first data to detect a relative movement of the capsule endoscope 13 with respect to the human body. Alternatively, the second analyzer 201 may analyze an image to detect a relative movement of the capsule endoscope 13 with respect to the human body.

The determiner 102 may select an analysis result to be used on the basis of the first analysis result, the second analysis result, and the third analysis result. For example, the determiner 102 selects an analysis result used for determining an imaging timing by using a method that is the same as the method in which the second analyzer 201 designates the analysis result by using the instruction data. For this reason, the second analyzer 201 need not generate instruction data. The first wireless transmitter 202 need not transmit instruction data. The first wireless receiver 104 need not receive instruction data.

The capsule endoscope system according to each aspect of the present invention need not have a configuration corresponding to at least one of the second movement sensor 2000, a battery remaining capacity estimator 2001, and a position estimator 2002.

As described above, the capsule endoscope 13 includes the third analyzer 107 configured to analyze an image acquired by the imager 103 and generate the third analysis result. The third analysis result is input to the determiner 102. The determiner 102 determines an imaging timing in the second period on the basis of any one of the first analysis result, the second analysis result, and the third analysis result.

The second analyzer 201 generates instruction data to designate any one of the first analysis result, the second analysis result, and the third analysis result on the basis of the second analysis result. The first wireless transmitter 202 further transmits the instruction data to the capsule endoscope 13. The first wireless receiver 104 further receives the instruction data from the wireless communication device 22. The instruction data is input to the determiner 102. The determiner 102 selects any one of the first analysis result, the second analysis result, and the third analysis result on the basis of the instruction data.

In the fourth embodiment, like in the first embodiment, the capsule endoscope system 1 can achieve both a rapid response to the movement of the capsule endoscope 13 and determining of a frame rate based on a plurality of analyses.

The third analyzer 107 can analyze the image to accurately detect the movement of the capsule endoscope 13. As a result, the determiner 102 can determine an imaging timing on the basis of the accurate movement of the capsule endoscope 13 with respect to the human body.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A capsule endoscope system, comprising:
   a capsule endoscope; and
   a wireless communication device,
   wherein the capsule endoscope comprises:

a first movement sensor configured to detect movement of the capsule endoscope and generate first data indicating the detected movement of the capsule endoscope;

one or more first processors, each comprising hardware, the one or more first processors being configured to:
analyze the first data and generate a first analysis result that is an analysis result of the first data;
determine an imaging timing; and
control imaging at the determined imaging timing; and a first wireless receiver configured to receive a second analysis result that is an analysis result of second data different in kind from the first data or detected from an object different from an object from which the first data is detected from the wireless communication device and output the second analysis result to the one or more first processors, the wireless communication device comprises:
one or more second processors, each comprising hardware, the one or more second processors being configured to analyze the second data and generate the second analysis result; and
a first wireless transmitter configured to transmit the second analysis result to the capsule endoscope, wherein the one or more first processors are further configured to:
output the first analysis result at a first period that is equal to or shorter than a reception period at which the first wireless receiver receives the second analysis result, and
determine the imaging timing at a second period that is equal to or shorter than the reception period on the basis of only one of the first analysis result and the second analysis result.

2. The capsule endoscope system according to claim 1, wherein the one or more second processors are further configured to generate instruction data to designate only one of the first analysis result and the second analysis result on the basis of the second analysis result,
the first wireless transmitter is further configured to transmit the instruction data to the capsule endoscope,
the first wireless receiver is further configured to receive the instruction data from the wireless communication device,
the instruction data is input to the one or more first processors, and
the one or more first processors are configured to select only one of the first analysis result and the second analysis result on the basis of the instruction data.

3. The capsule endoscope system according to claim 1, wherein the wireless communication device further includes a second movement sensor configured to detect movement of a human body in which the capsule endoscope is placed and generate the second data indicating the detected movement of the human body.

4. The capsule endoscope system according to claim 3, wherein the capsule endoscope further includes a second wireless transmitter configured to transmit the first data to the wireless communication device,
the wireless communication device further includes a second wireless receiver configured to receive the first data from the capsule endoscope, and
the one or more second processors further analyze the first data and the second data and generate the second analysis result that is an analysis result of the first data and the second data.

5. The capsule endoscope system according to claim 1, wherein the capsule endoscope further includes a second wireless transmitter configured to transmit the image to the wireless communication device,
the wireless communication device further includes a second wireless receiver configured to receive the image from the capsule endoscope,
the one or more second processors further analyze the image, and
the image is the second data.

6. The capsule endoscope system according to claim 1, wherein the capsule endoscope further includes a battery configured to supply electric power to the first movement sensor, the one or more first processors and the first wireless receiver, and
the one or more second processors are further configured to receive an estimate of a remaining capacity of the battery and generate the second data indicating the estimated remaining capacity.

7. The capsule endoscope system according to claim 1, wherein the one or more second processors are further configured to receive an estimate of a position of the capsule endoscope and generate the second data indicating the estimated position.

8. The capsule endoscope system according to claim 1, wherein the one or more first processors are further configured to:
analyze an acquired image and generate a third analysis result that is an analysis result of the image,
determine the imaging timing at the second period on the basis of only one of the first analysis result, the second analysis result, and the third analysis result.

9. The capsule endoscope system according to claim 1, wherein the first period is shorter than the reception period.

* * * * *